United States Patent
Hayashi

(10) Patent No.: US 6,974,215 B2
(45) Date of Patent: Dec. 13, 2005

(54) OPTICAL INSTRUMENT

(75) Inventor: Takefumi Hayashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 293 days.

(21) Appl. No.: 10/343,327

(22) PCT Filed: Aug. 8, 2001

(86) PCT No.: PCT/JP01/06813

§ 371 (c)(1),
(2), (4) Date: Jul. 9, 2003

(87) PCT Pub. No.: WO02/11611

PCT Pub. Date: Feb. 14, 2002

(65) Prior Publication Data

US 2005/0018136 A1    Jan. 27, 2005

(30) Foreign Application Priority Data

Aug. 9, 2000 (JP) .............................. 2000-241394

(51) Int. Cl.[7] .............................................. A61B 3/10
(52) U.S. Cl. ..................................... 351/212; 351/211
(58) Field of Search ........................... 251/200, 205, 251/206, 211, 212, 213, 214, 221, 246; 600/558

(56) References Cited

U.S. PATENT DOCUMENTS 5,684,562 A * 11/1997 Fujieda ........................ 351/212
5,907,388 A *  5/1999 Fujieda ........................ 351/211
6,190,011 B1 *  2/2001 Fujieda ........................ 351/206
6,224,213 B1 *  5/2001 Kobayashi .................... 351/212

FOREIGN PATENT DOCUMENTS

| JP | 4-505411    | 9/1992  |
| JP | 8-164113    | 6/1996  |
| JP | 11-137520   | 5/1999  |
| JP | 2000-70222  | 3/2000  |
| JP | 2000-296110 | 10/2000 |
| JP | 2000-308617 | 11/2000 |
| JP | 2001-46340  | 2/2001  |
| JP | 2001-120503 | 5/2001  |
| JP | 2001-269314 | 10/2001 |

* cited by examiner

Primary Examiner—Brian L. Casler
Assistant Examiner—John R. Sanders
(74) Attorney, Agent, or Firm—Armstrong, Kratz, Quintos, Hanson & Brooks, LLP

(57) ABSTRACT

An optical instrument comprising an eye refractive power measurement index optical system (50) for projecting an eye refractive power index in order to measure the refractive power of an eye (E) to be examined, a fixed index projecting optical system (10) for fixing/fogging the eye (E), an observation optical system (40) for observing the eye (E), a light receiving optical system (60), a ring plate (30) and an infrared LED (34) for projecting a cornea shape index used to measure the cornea shape of the eye (E), a ring plate (80) and an infrared LED (84) for projecting light to the center of the cornea via an objective lens (22), and an alignment index projecting optical system (70), whereby it is possible to project part of the cornea shape index onto the cornea (Ec) of the eye to be examined via the objective lens (22) of the observation optical system (40) for observation.

6 Claims, 7 Drawing Sheets

OPTICAL INSTRUMENT

CROSS-REFERENCES TO RELATED APPLICATIONS

This application claims priority from Japanese Application No. 2000-241394, filed Aug. 9, 2000, and is a national-stage entry of International Application No. PCT/JP01/06813, filed Aug. 8, 2000.

TECHNICAL FIELD

The present invention relates to an ophthalmologic apparatus, and more particularly to an ophthalmologic apparatus for projecting an index to the cornea of an eye to be examined to conduct cornea measurement.

BACKGROUND ART

Conventionally, in order to measure a cornea shape with precision, a cornea shape measuring apparatus for projecting an index, for example, a Placido's pattern to the cornea of an eye to be examined has been known.

Note that "cornea shape measurement" in this specification includes not only cornea mapping measurement for a central cornea shape of a cornea central region, a peripheral cornea shape of a cornea peripheral region, or the like but also measurement for, for example, a corneal curvature radius, a corneal astigmatic, or a corneal astigmatic axial angle.

On the other hand, an eye refractive power measuring apparatus which is called a so-called refractometer has been known as an apparatus for measuring eye refractive power of an eye to be examined.

In general, data and the like related to a cornea shape and eye refractive power are important data for conducting suitable diagnosis, and it is desirable that these data are obtained by measurement using a single apparatus. In addition, there is a demand to reduce an occupying space of an apparatus. In view of such requirements, in recent years, an ophthalmologic apparatus of a type having a complex function which is provided with both a function for measuring a cornea shape and a function for measuring eye refractive power, which are described above, also makes its appearance.

According to such an ophthalmologic apparatus, a circular hole portion is formed in a central region of a Placido's plate for forming, for example, a Placido's pattern, and then an index light flux for eye refractive power measurement is projected through the hole portion and reflected light from an eye fundus is received through the hole portion so that cornea shape data and eye refractive power data can be obtained by a single apparatus.

Now, when a cornea shape is analyzed, it is desirable that a measurement area of the cornea shape can be made to extend to the vicinity of a cornea central portion. For example, it is desirable that a ring pattern of Φ 1.0 is projected onto a cornea and cornea shape measurement based on the ring pattern is conducted. Therefore, it is considered that a smallest ring on the above-mentioned Placido's plate is further made smaller to make the hole portion small.

However, when the hole portion is made to a predetermined size or smaller, projection and receipt of a light flux for eye refractive power measurement are inhibited. Thus, when a measurement area of a cornea shape measuring apparatus is increased, there is a possibility that a reduction in measurement sensitivity of eye refractive power is caused and an erroneous measurement result is calculated so that misdiagnosis of an examiner is induced.

As described above, there is a limitation with respect to the measurement area of the cornea shape so that the vicinity of the cornea central region cannot be measured.

The present invention has been made in view of the above circumstances, and an object thereof is to provide an ophthalmologic apparatus which can measure a cornea shape in the vicinity of a cornea central region without blocking a light flux for measuring eye refractive power and accurately measure the eye refractive power.

DISCLOSURE OF THE INVENTION

In order to achieve the above-mentioned object, according to the present invention, an ophthalmologic apparatus is characterized by including: cornea shape index projecting means for projecting a cornea shape index for measuring a cornea shape of an eye to be examined to a cornea of the eye to be examined; an observation optical system for measuring the cornea shape based on an index reflection image reflected on the eye to be examined and observing the eye to be examined; and an eye refractive power measurement index optical system partially using an optical path of the observation optical system, for projecting an eye refractive power measurement index for measuring eye refractive power of the eye to be examined to the eye to be examined through the used optical path, in which the cornea shape index projecting means includes: first projecting means for projecting a first index as a part of the cornea shape index to a peripheral region of the cornea; and second projecting means for projecting a second index as another part of the cornea shape index to a central region of the cornea through the optical path used for at least both the eye refractive power measurement index optical system and the observation optical system.

Further, according to the present invention, it is characterized in that the first index in the first projecting means is formed from a first ring pattern composed of a plurality of rings with a substantially concentric shape, and that the second index in the second projecting means is formed from a second ring pattern composed of a ring with a smaller diameter than at least a smallest diameter ring of the first ring pattern.

Further, according to the present invention, it is characterized in that the first projecting means includes a first plate for forming the first index, and that the first plate has a hole portion which allows to transmit a light flux for measuring the eye refractive power in the central region.

Further, according to the present invention, it is characterized in that the second projecting means includes a second plate for forming the second index, which is disposed on the optical path of the observation optical system, and that the second plate has a hole portion which allows to transmit an optical axis of the index reflection image in a central region.

Further, according to the present invention, it is characterized in that a lens is disposed opposite to the hole portion of the first plate on the optical path used for the eye refractive power measurement index optical system and the observation optical system, and that the second projecting means conducts projection to the central region of the cornea through the lens.

Further, according to the present invention, it is characterized in that the second plate of the second projecting means includes at least one ring pattern light transmitting portion, and that the ring pattern light transmitting portion is formed such that its diameter becomes at least 1.0 mm or less on the eye to be examined.

BEST MODE FOR CARRYING OUT THE INVENTION

Hereinafter, an example of a preferred embodiment mode of the present invention will be specifically described with reference to the drawings.

(Schematic Explanation)

Figure 1:
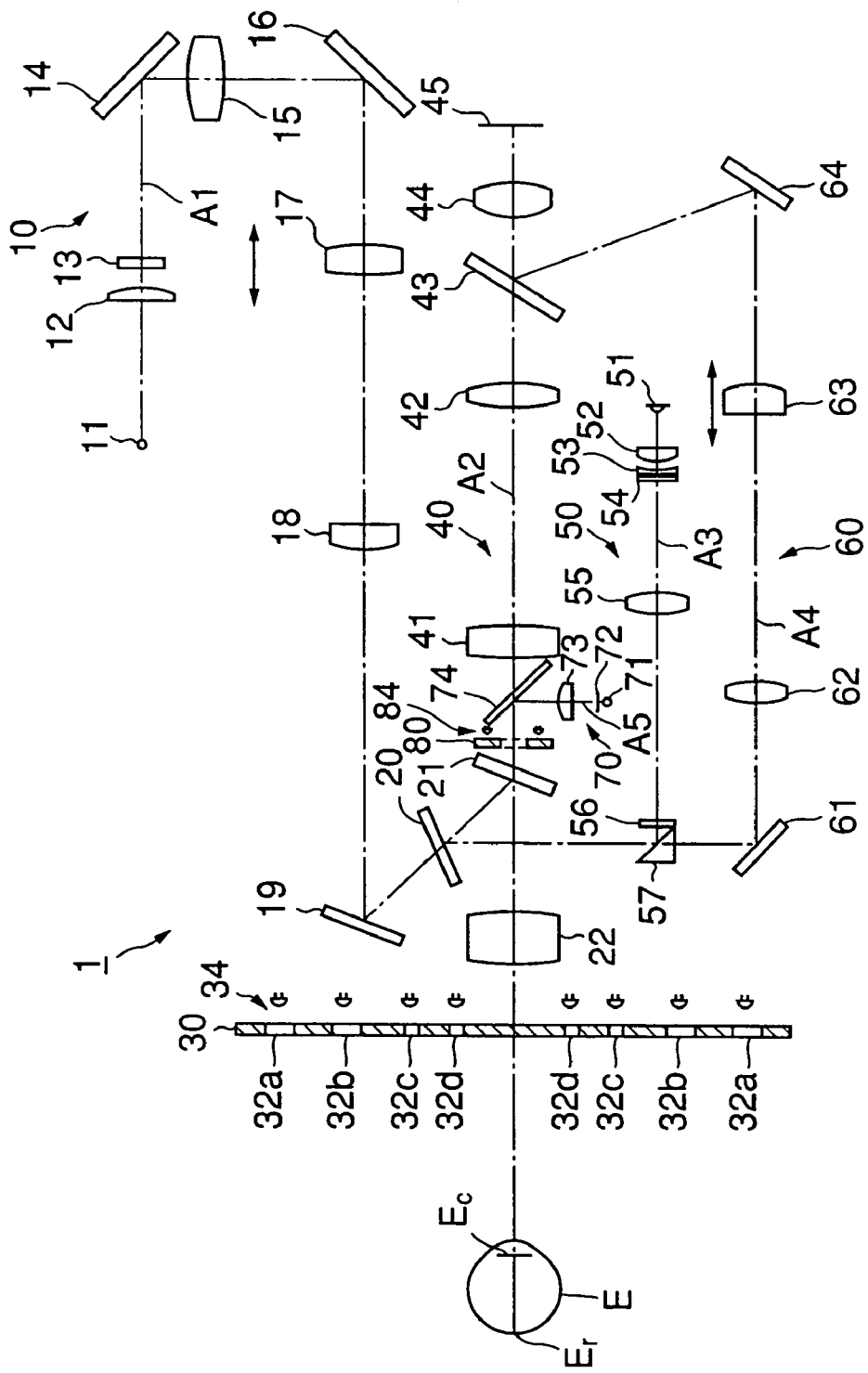
FIG. 1 is an explanatory view showing an optical system of an ophthalmologic apparatus of the present invention.

First, a schematic structure of an entire ophthalmologic apparatus of the present invention will be described with reference to FIG. 1. FIG. 1 is an explanatory view showing the ophthalmologic apparatus of this example.

An ophthalmologic apparatus 1 of this example has a function for projecting a plurality of ring patterns to a cornea Ec of an eye to be examined E and measuring a shape of the cornea Ec based on a plurality of ring reflection images reflected on the eye to be examined E and a function for measuring eye refractive power of the eye to be examined E.

Specifically, as shown in FIG. 1, the ophthalmologic apparatus 1 is constructed to include a fixed index projecting optical system 10 for projecting a fixed index to the eye to be examined E to conduct fogging, a ring plate 30 for projecting an index C1 to C4 (first index) which is a part of a cornea shape index as described later to a peripheral region of the cornea Ec, an observation optical system 40 for observing an anterior eye portion of the eye to be examined E to conduct alignment and to measure a cornea shape based on index reflection images reflected on the eye to be examined E, an eye refractive power measurement index optical system 50 for projecting an eye refractive power measurement index using measurement light for measuring eye refractive power to an eye fundus Er of the eye to be examined E to objectively measure the eye refractive power of the eye to be examined E, a light receiving optical system 60 for receiving the measurement light reflected on the eye fundus Er, an alignment index projecting optical system 70 for projecting an alignment mark M which is an index for alignment and described later, and a ring plate 80 for projecting an index C6 (second index, for example, a Placido's pattern which is a concentric ring pattern) which is a part of the cornea shape index for measuring the cornea shape to the cornea Ec of the eye to be examined E and described later, to a central region of the cornea Ec.

Note that, in this example, eye refractive power measuring means is composed of the fixed index projecting optical system 10, the eye refractive power measurement index optical system 50, and the light receiving optical system 60. First projecting means is composed to further include the ring plate 30, and second projecting means is composed to further include the ring plate 80. Cornea shape index projecting means is composed of the first projecting means and the second projecting means. The cornea shape index projecting means is to project the cornea shape index (C1 to C4 and C6 as described later) for measuring the cornea shape of the eye to be examined E to the cornea Ec of the eye to be examined E.

Therefore, a part of the cornea shape index for measuring the cornea shape is projected to the cornea Ec of the eye to be examined E through an objective lens 22 (the detail will be described later) of the observation optical system 40 for conducting observation and alignment. Hereinafter, each of these optical systems will be described.

(Fixed Index Projecting Optical System)

As shown in FIG. 1, the fixed index projecting optical system 10 is composed by disposing a lamp 11 as a light source, a collimator lens 12, a fixed index plate 13, a reflection mirror 14, a collimator lens 15, a reflection mirror 16, a movable lens 17, a relay lens 18, a reflection mirror 19, dichroic mirrors 20 and 21, and the objective lens 22 on an optical path A1.

In the fixed index projecting optical system 10, a light flux emitted from the lamp 11 passes through the collimator lens 12 and illuminates the fixed index plate 13. The light flux exited from the fixed index plate 13 is reflected by the reflection mirror 14, and then reflected by the reflection mirror 16 through the collimator lens 15, reflected by the reflection mirror 19 through the movable lens 17 and the relay lens 18, transmits through the dichroic mirror 20, reflected by the dichroic mirror 21, and projected to the eye to be examined E through the objective lens 22.

Note that the fixed index plate 13 is located conjugate with the eye fundus Er. Marks which become the fixed marks (for example, a scene chart and a star burst chart which are not shown) are formed to the fixed index plate 13. The marks are projected to the eye fundus Er. By the projection of the marks, the eye to be examined E is faced in a predetermined direction and fogged.

Also, the objective lens 17 is moved in the direction of the optical axis A1 to fog the eye to be examined E. The movement is conducted by controlling a relay lens actuating mechanism which is not shown by a control system as described later.

(Observation Optical System)

The observation optical system 40 is composed by disposing a hole portion 33 of the ring plate 30, the objective lens 22, the dichroic mirror 21, a hole portion 83 of the ring plate 80, a dichroic mirror 74, relay lenses 41 and 42, a dichroic mirror 43, a CCD lens 44, and a CCD 45 as image pickup means on an optical path A2.

A light flux forming an image of the anterior eye portion transmits the dichroic mirror 21 through the objective lens 22, and is imaged by the CCD lens 44 through the dichroic mirror 74, the relay lenses 41 and 42, and the dichroic mirror 43 so that a anterior eye portion reflection image is imaged on the CCD 45.

Then, the anterior eye portion is displayed on a monitor 202 (see FIG. 8) as display means and it is used for alignment between the optical axis of the apparatus and the eye to be examined E.

(Eye Refractive Power Measurement Index Optical System)

The eye refractive power measurement index optical system 50 is composed by disposing an infrared LED 51 as a light source, a collimator lens 52, a conical prism 53, a ring-shaped index 54, a relay lens 55, a ring-shaped stop 56, a hole prism 57, the dichroic mirrors 20 and 21, and the objective lens 22 on an optical path A3.

In the eye refractive power measurement index optical system 50, a light flux emitted from the infrared LED 51 is irradiated to the ring-shaped index 54 as an eye refractive power measurement index through the collimator lens 52 and the conical prism 53. The light flux exited from the ring-shaped index transmits through the relay lens 55, and the light flux is stopped down by the ring-shaped stop 56. The stopped-down light flux is reflected by the hole prism 57, reflected by the dichroic mirror 20, and reflected also by the dichroic mirror 21. Thus, the ring-shaped index 54 is projected to the eye fundus Er of the eye to be examined E through the objective lens 22.

Here, the infrared LED 51 is to emit light having the near infrared region. In addition, the conical prism 53 is a member for converting light which is emitted from the infrared LED 51 and changed to a parallel light flux by the collimator lens 52 into a ring light flux. The infrared LED 51 and the ring-shaped stop 56 become optically conjugate with each other by the relay lens 55.

Figure 7:
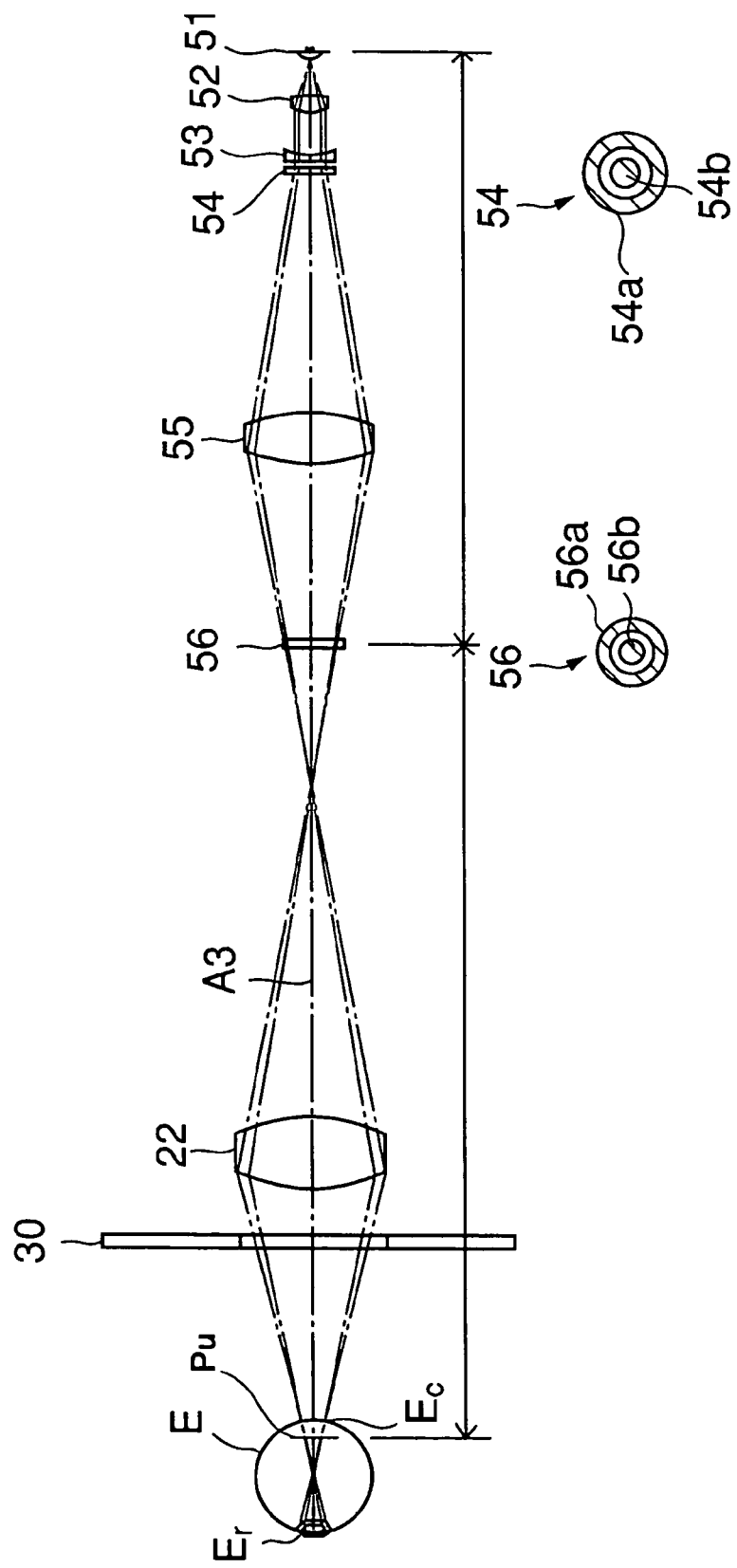
FIG. 7 is an explanatory view showing a measurement projection light flux of eye refractive power in the ophthalmologic apparatus of the present invention.

Further, as shown in FIG. 7, the ring-shaped stop 56 is composed of a ring-shaped ring pattern light transmitting portion 56b and a light shielding portion 56a. In addition, the ring-shaped index 54 is composed of a ring-shaped ring pattern light transmitting portion 54b and a light shielding portion 54a. The ring-shaped stop 56 and a pupil Pu of the eye to be examined are located optically conjugate with each other with respect to the objective lens 22. Then, a ring image formed by light which transmits through the ring pattern light transmitting portion 54b of the ring-shaped index 54 is stopped down by the ring-shaped stop 56 and projected to the eye fundus Er.

(Light Receiving Optical System)

The light receiving optical system 60 is composed by disposing the objective lens 22, the dichroic mirrors 20 and 21, the hole prism 57, a reflection mirror 61, a relay lens 62, a movable lens 63, a reflection mirror 64, the dichroic mirror 43, the CCD lens 44, and the CCD 45 on an optical path A4.

In the light receiving optical system 60, a light flux reflected on the eye fundus Er transmits through the objective lens 22, reflected by the dichroic mirror 20, reflected by the dichroic mirror 21, passes through the hole portion of the hole prism 57, reflected by the reflection mirror 61, reflected by the reflection mirror 64 through the relay lens 62 and the movable lens 63, reflected by the dichroic mirror 43, passes through the CCD lens 44, and projected to the CCD 45. Based on the amount of movement of the movable lens 63 in the direction of the optical axis A4, eye refractive power can be obtained.

Of the ring-shaped index light projected to the eye fundus Er, a reflection light flux from the eye fundus is imaged on the CCD 45 through the light receiving optical system 60 so that the ring image is formed. The eye refractive power is obtained from the ring image by the calculation of a control circuit 209 (see FIG. 8) as described later.

(Alignment Index Projecting Optical System)

The alignment index projecting optical system 70 is composed by disposing an infrared LED 71 as a light source, a stop 72, a relay lens 73, and the dichroic mirror 74 on an optical path A5.

A light flux emitted from the infrared LED 71 is illuminated to the stop 72 as an index for alignment. The light flux from the stop 72 is reflected by the dichroic mirror 74 through the relay lens 73. The reflected light flux is projected to the cornea Ec of the eye to be examined E through the dichroic mirror 21 and the objective lens 22. The light flux reflected on the cornea Ec passes on the optical path A2 and is projected onto the CCD 45.

(With Respect to Ring Plate in First Projecting Means)

Figure 2:
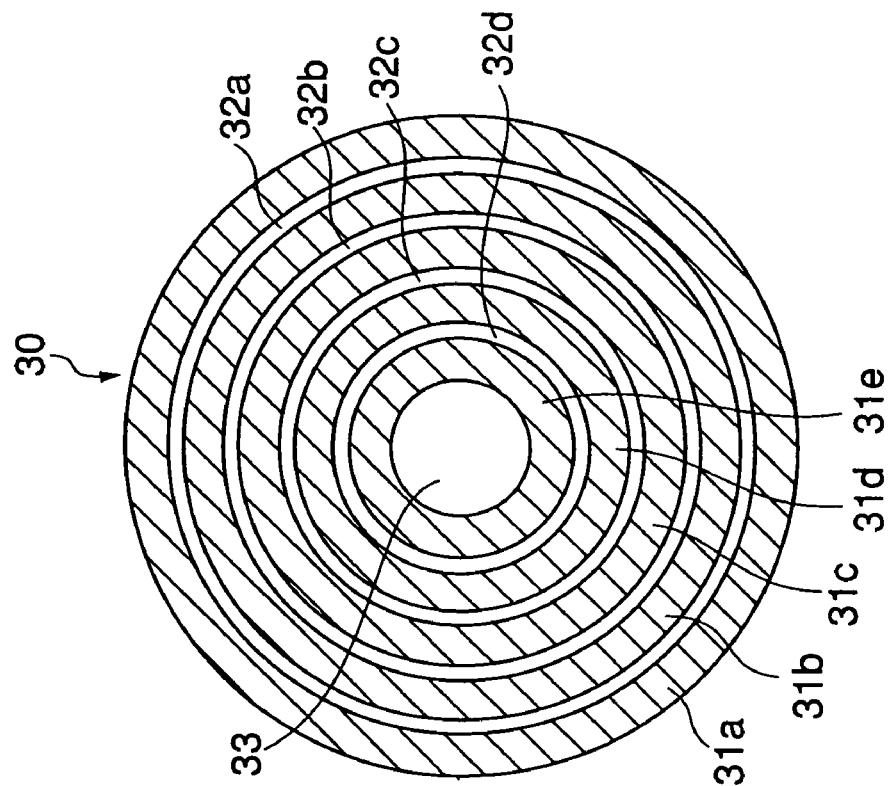
FIG. 2(A) and FIG. 2(B) are explanatory views showing a ring plate of the ophthalmologic apparatus of the present invention, and (A) is a cross sectional view of (B).
Figure 2:
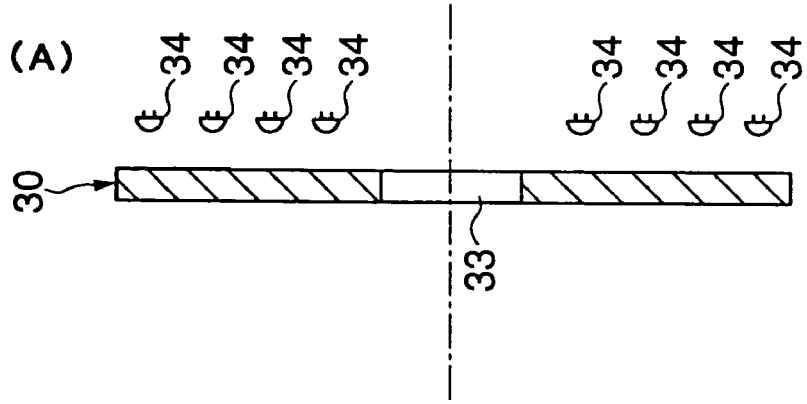

Next, a specific structure of the above-described ring plate 30 which is a portion of the feature of the present invention and the first projecting means of this example will be described using FIG. 2.

In this example, the first projecting means is constructed by a structure including the ring plate 30 and infrared LEDs 34 concentrically arranged along a ring pattern as the first index which is formed to the ring plate 30.

As shown in FIG. 2(B), the ring plate 30 is constructed to include a plurality of concentrically formed ring pattern light transmitting portions 32 (32a to 32d) for diffusing and transmitting light, which is made from a diffusion plate formed in a substantially circular shape, a ring pattern light shielding portion 31 (31a to 31e) for light shielding, and a hole portion 33 formed in the central portion of the ring plate 30. When light is diffused from and transmitted through the plurality of ring pattern light transmitting portions 32 (32a to 32d), the ring-pattern-shaped index C1 to C4 (first index) can be directly projected onto the eye to be examined E.

Also, the hole portion 33 is formed in a size such that the light flux which transmits through the objective lens 22 between the eye refractive power measurement index optical system 50 and the eye to be examined E, the respective light fluxes from other various optical systems, and the like are allowed to transmit. In particular, measurement sensitivity in eye refractive power measurement is determined according to a light flux diameter on the eye to be examined E. Thus, when the measurement sensitivity is to be improved, it is necessary to maximize the diameter of the objective lens 22 as much as possible. Accordingly, when the hole portion 33 is also formed in a diameter size such that the light flux from the objective lens 22 can sufficiently transmit, high measurement sensitivity can be kept.

Note that, with respect to the number of ring pattern light transmitting portions 32 (32a to 32d), the example in which plural items, for example, 4 items are formed is shown in FIG. 2(B). However, it is not limited to this example. Plural items, for example, 5 items, 6 items, or 8 items may be formed. Further, an interval between the respective ring pattern light transmitting portions can be also made wide or narrow according to locations. For example, the even ring pattern light transmitting portions are made thick and the odd ring pattern light transmitting portions are made thin. Thus, with respect to a display mode (projection mode), a line is made thick in a portion corresponding to a large scale and a line is made thin in a small scale portion so that easily viewable display may be obtained. In addition, it may be constructed such that an interval between the respective ring pattern light transmitting portions is increased as those locations are shifted to the outer portion.

As shown in FIG. 2(A), it is preferable that a plurality of infrared LEDs 34 which are located in the rear surface position of the ring plate 30 as the diffusion plate and arranged corresponding to the ring pattern light transmitting portions 32 (32a to 32d) are used as light sources for light which is diffused from and transmitted through the ring pattern light transmitting portions 32 (32a to 32d). Note that, in the cross sectional view shown in FIG. 2(A), 4 items are provided above and below the hole portion 33 taken as the center, that is, 8 items in total are provided. Actually, the infrared LEDs 34 are arranged in a ring shape corresponding to the ring-shaped ring pattern light transmitting portions 32 (32a to 32d) shown in FIG. 2(B). In addition, the infrared LEDs 34 have a function for illuminating the anterior eye portion of the eye to be examined E through the ring pattern light transmitting portions 32.

(With Respect to Ring Plate in Second Projecting Means)

Next, a specific structure of the above-described ring plate 80 which is the feature of the present invention will be also described in detail.

In this example, the second projecting means is constructed by a structure including the ring plate 80 and infrared LEDs 84 circularly arranged along a Placido's pattern formed to the ring plate 80.

Figure 3:
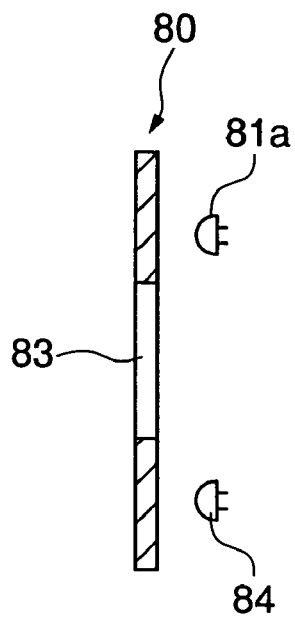
FIG. 3(A) and FIG. 3(B) are explanatory views showing a ring plate of the ophthalmologic apparatus of the present invention, and (A) is a cross sectional view of (B).
Figure 3:
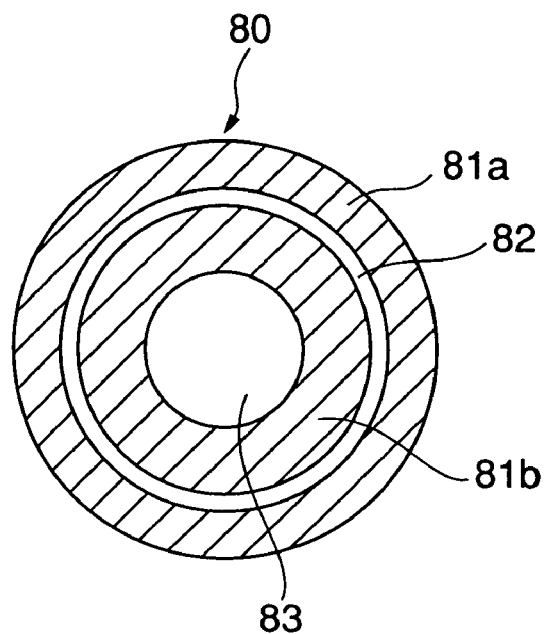

As shown in FIGS. 3(A) and 3(B), the ring plate 80 is formed in a substantially circular shape as in the ring plate 30 in structure, made from a flat diffusion plate located in a focal position of the objective lens 22, and is obtained by conducting multiple ring printing on the surface of the diffusion plate. The ring plate 80 is constructed to include one or a plurality of concentrically formed ring pattern light transmitting portions 82 for diffusing and transmitting light of a ring pattern having a predetermined width, a ring pattern light shielding portion 81 for ring pattern light shielding, and a circular hole portion 83 formed in the central portion.

The ring pattern light transmitting portions 82 is, for example, a portion to which a coating is not applied, of a portion formed from a white coating layer and a black coating layer which are applied on the surface of the diffusion plate.

With respect to the diameter of the ring pattern light transmitting portions 82, it is desirable that the diameter of the ring pattern projected onto the eye to be examined E becomes at least 1.0 mm or less. Thus, an accurate cornea shape in a cornea central region can be measured.

It is preferable that a size of the hole portion 83 formed on the central portion is set to the extent to which the light flux forming the anterior eye portion image can be sufficiently ensured to the CCD 45 of the observation optical system 40. Further, the hole is located in a focal position of the objective lens so that it has a so-called telecentric stop function.

When the light is diffused from and transmitted through the ring pattern light transmitting portions 82, as displayed on a display screen 100 (monitor screen) described later, the ring-pattern-shaped index C6 (second index) (see FIG. 5) can be projected onto the eye to be examined E and its reflection image can be displayed. Note that, with respect to the number of ring pattern light transmitting portions 82, the example in which, for example, 1 item is formed as shown in FIG. 3(B) is described. However, it is not limited to this example. Plural items, for example, 2 items, 3 item, 4 items, . . . or the like may be formed. Further, when plural items are formed, an interval between the respective ring pattern light transmitting portions can be also made wide or narrow according to locations. For example, the even ring pattern light transmitting portions are made thick and the odd ring pattern light transmitting portions are made thin. Thus, with respect to a display mode (projection mode), a line may be made thick in a portion corresponding to a large scale and a line may be made thin in a small scale portion.

In addition, it may be constructed such that an interval between the respective ring pattern light transmitting portions is increased as those locations are shifted to the outer portion.

As shown in FIG. 3(A), it is preferable that a plurality of infrared LEDs 84 which are located in the rear surface position of the ring plate 80 as the diffusion plate and arranged corresponding to the ring pattern light transmitting portions 82 are used as light sources for light which is diffused from and transmitted through the ring pattern light transmitting portions 82.

Figure 4:
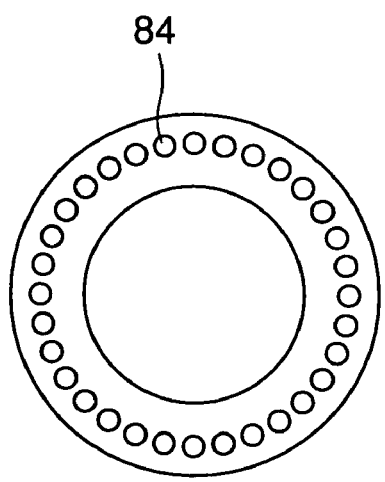
FIG. 4 is an explanatory view showing an infrared LED of the ophthalmologic apparatus of the present invention.

The infrared LEDs 84 are near infrared region illumination lamps, arranged opposite to the ring pattern light transmitting portion 82d, and attached to a PC plate which is not shown. The not-shown PC plate is held to, for example, a unit base and its surface becomes white so that red light is reflected forward. Note that, in the cross sectional view shown in FIG. 3(A), 1 item is provided above and below the hole portion 83 taken as the center, that is, 2 items in total are provided. Actually, as shown in FIG. 4, the infrared LEDs 84 are arranged in a ring shape corresponding to the ring-shaped ring pattern light transmitting portions 82 shown in FIG. 3(B).

According to the structure of the hole portion 33 of the ring plate 30 and the structure of the hole portion 83 of the ring plate 80 which are described above, first, a light flux from the plurality of infrared LEDs 34 which transmits through the ring pattern light transmitting portions 32 of the ring plate 30 is projected as a ring pattern for measuring a cornea peripheral region to the cornea Ec of the eye to be examined E. Then, the reflection light flux of the ring pattern which is reflected on the cornea Ec is projected onto the CCD 45 through the optical path A2 of the observation optical system 40.

In addition, a light flux from the plurality of infrared LEDs 84 which transmits through the ring pattern light transmitting portions 82 of the ring plate 80 is projected as the ring pattern for measuring the cornea peripheral region to the cornea Ec of the eye to be examined E through the dichroic mirror 21 and the objective lens 20. Then, the reflection light flux of the ring pattern which is reflected on the cornea Ec is projected onto the CCD 45 through the optical path A2 of the observation optical system 40.

Figure 5:
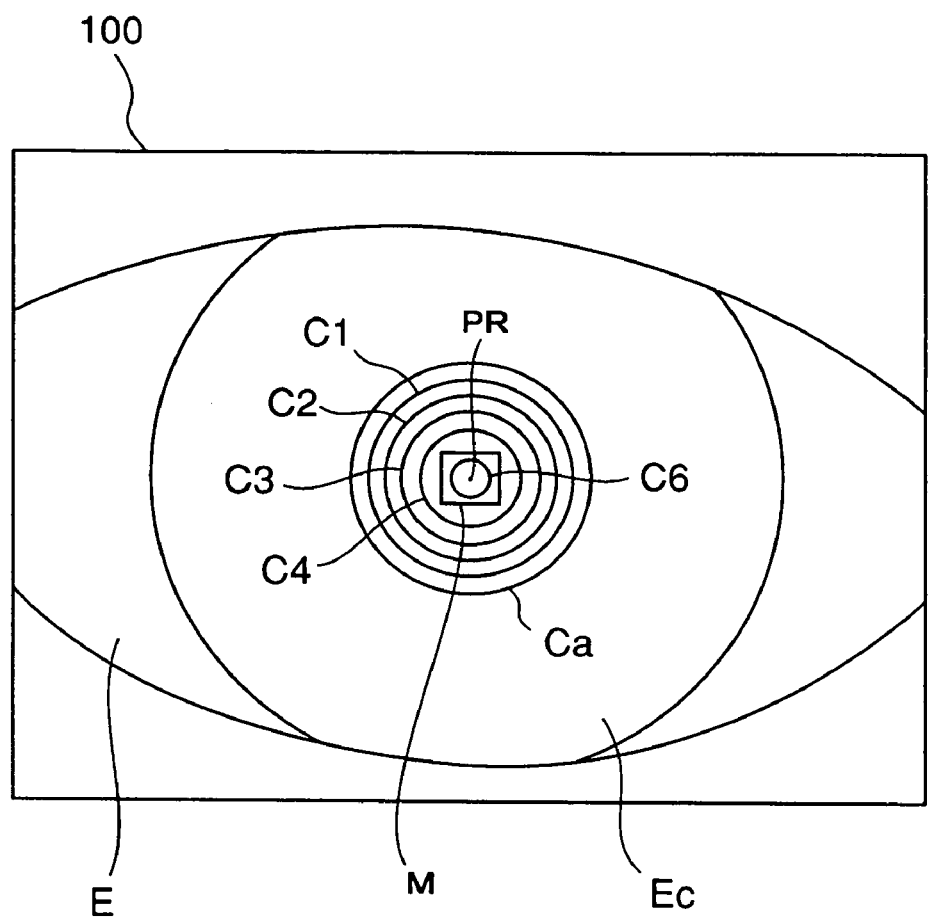
FIG. 5 is an explanatory view showing a display screen of the ophthalmologic apparatus of the present invention.

Therefore, the first index (C1 to C4) and the second index C6 as cornea shape indexes are formed on the display screen 100 (see FIG. 5).

(With Respect to Display Screen)

The index images C1 to C4 (first index) and C6 (second index) as shown in FIG. 5 are displayed on the monitor 202 as display means of the ophthalmologic apparatus of this example. In other words, on the display screen 100 of the monitor 202, the eye to be examined E is displayed and further the indexes C1 to C4 and C6 are displayed on the eye to be examined E. Note that, in FIG. 5, Ca denotes the contour of the outer edge of the cornea Ec and C1 to C4 and C6 denote the indexes.

The indexes C1 to C4 and C6 are composed to include the first index C1 to C4 displayed according to the above-mentioned first projecting means and the second index C6 displayed according to the second projecting means.

A ring pattern C1 to C4 as the first index indicates a cornea reflection image projected through the above-mentioned ring plate 30. M denotes an alignment mark formed by an image synthesizing circuit which is not shown. A ring pattern C6 as the second index indicates a cornea reflection image projected through the ring plate 80. In addition, PR denotes a cornea reflection image of an alignment index 72 projected by the alignment index projecting optical system 70.

Thus, according to this example, fine indexes are formed in the cornea central region as compared with a conventional case so that more accurate cornea shape measurement becomes possible.

Note that, although not shown, in other modes, corneal curvature radius measurement data and eye refractive power measurement data are synthetically displayed on the display screen 100.

(With Respect to Control System)

Figure 8:
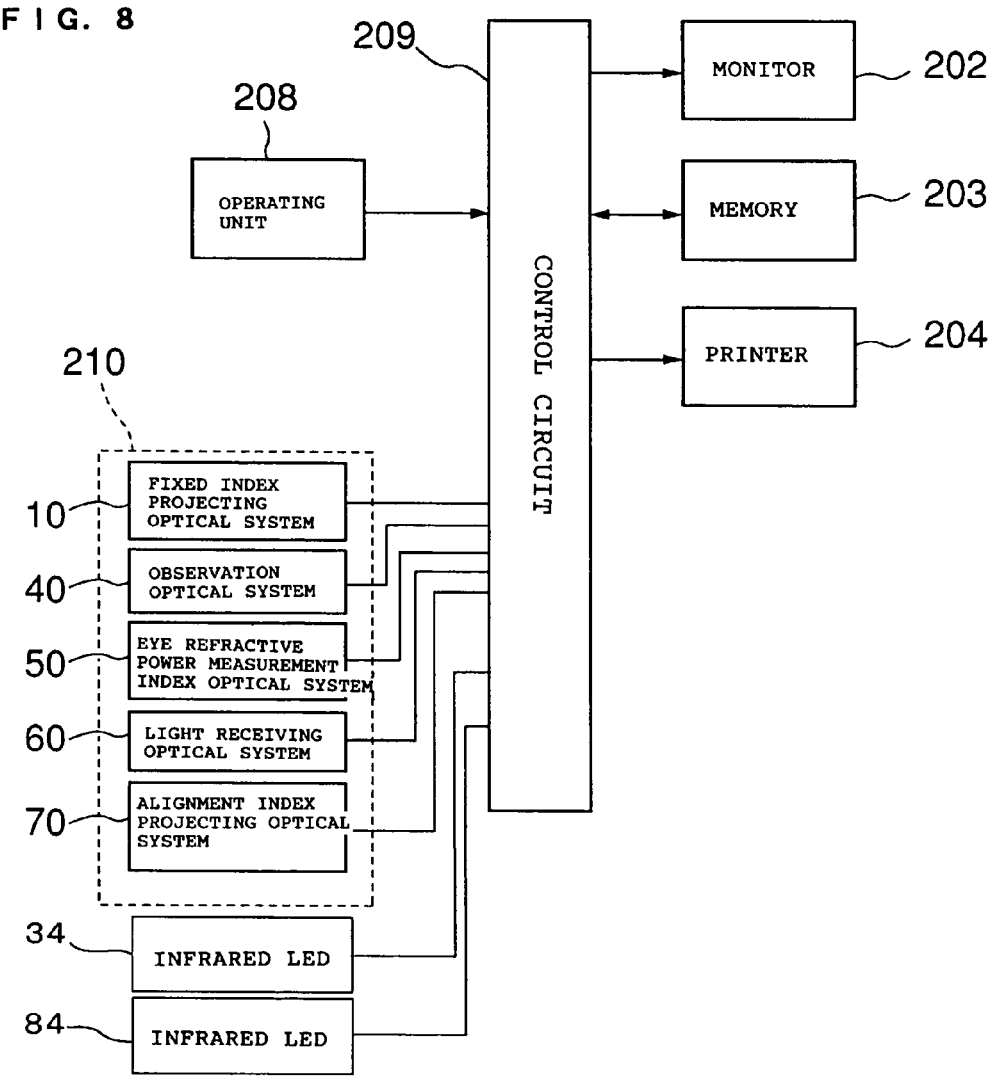
FIG. 8 is a functional block diagram showing a control system of the ophthalmologic apparatus of the present invention.

In FIG. 8, a functional block diagram showing a configuration of a control system in the ophthalmologic apparatus as described above is disclosed.

An ophthalmologic apparatus 1 of this example is constructed to include: the monitor 202 as display means for displaying images of the eye to be examined E and the like, the indexes C1 to C4 and C6 (ring pattern image and Placido's ring projection image), measurement-related information such as eye refractive power and a cornea shape, and the like, from the CCD 45 of the observation optical system 40; a memory 203 as storage means for storing the images of the eye to be examined and the like, the indexes C1 to C4 and C6 (ring pattern image and Placido's ring projection image), the measurement related information such as the eye refractive power and the cornea shape, and various information such as control program information for controlling the entire ophthalmologic apparatus 200; a printer 204 as printing means for printing images and various data which are displayed on the display means 202; an operating unit 208 to be operated by an examiner; optical measurement means 210 including the various optical systems (10, 40, 50, 60, and 70) and the infrared LEDs 34 and 84 included in the cornea shape index projecting means, which are described above; and the control circuit 209 for conducting these controls and various computations.

Note that the operating unit 208 is composed to include; for example, a control lever for conducting positioning and focusing; and a control switch having various switches such as, a mode switching switch for switching among various modes such as an eye refractive power measurement mode, a cornea shape image display mode, and a mode for simultaneously measuring a corneal curvature radius and eye refractive power, a print switch for conducting print outputting, and a measurement switch.

The control circuit 209 has a function for computing a cornea shape, a corneal curvature radius, and the like from the indexes C1 to C4 and C6 of the images stored in the memory 203 (see FIG. 5).

In this case, in FIG. 8, a cornea shape measuring apparatus for measuring a cornea shape is composed of the infrared LEDs 34 and 84, the observation optical system 40, and the control circuit 209.

Also, the control circuit 209 controls the printer 204 and the like according to the operation of the operating unit 208. Further, the control circuit 209 computes eye refractive power from a ring image projected to the eye fundus Er.

According to the ophthalmologic apparatus 1 provided with such a control system, when an examiner conducts operations using the operating unit 208, the eye to be examined, of a person to be examined is displayed on the monitor 202. Further, operation such as alignment is conducted according to the operation of the operating unit 208 (detail will be described later).

(With Respect to Operations)

Next, operations of the ophthalmologic apparatus with the configuration as described above will be described with reference to FIGS. 1 to 8.

First, when a cornea shape of the eye to be examined E is measured, an examiner conducts alignment while viewing a cornea image of the anterior eye portion of the eye to be examined E which is displayed on the display screen 100 of the monitor 202. Here, as shown in FIG. 5, the alignment mark M for alignment is electrically displayed on the display screen 100.

The operating unit 208 is operated such that the cornea reflection image of the stop 72 which is projected on the optical path A5 shown in FIG. 1 is aligned with the center of the alignment mark M. Note that, when the anterior eye portion is observed, a part of the infrared LEDs 34 is used.

When the alignment is completed and the examiner operates the operating unit 208, the image shown in FIG. 5 is stored in the memory 203.

Then, a light flux of a ring reflection image resulting from reflection on the cornea Ec of the eye to be examined E is imaged into the CCD 45 together with an anterior eye portion image through the objective lens 22 on the optical axis A2.

Here, light fluxes from the respective ring plates 80 and 30 will be described. The light flux through the pattern of the ring plate 80 transmits through the dichroic mirror 21 and projected to the cornea Ec through the objective lens 22. The light flux reflected on the cornea Ec transmits through the objective lens 22 and the dichroic mirror 21, passes through the hole portion of the ring plate 80, and travels toward the CCD 45.

Figure 6:
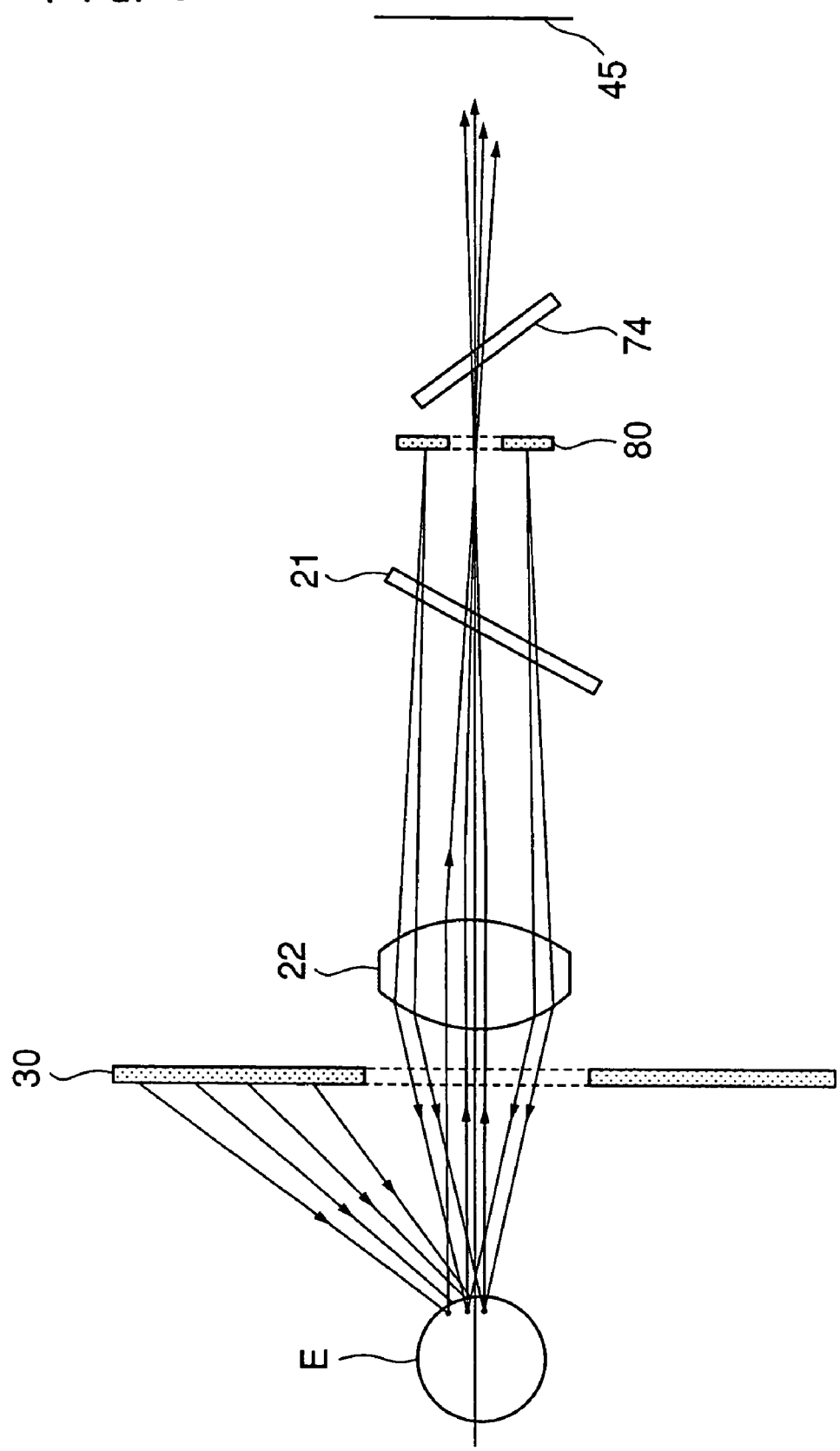
FIG. 6 is an explanatory view showing an illumination light flux by the ring plate in the ophthalmologic apparatus of the present invention.

Also, as shown in FIG. 6, a light flux exited from the pattern of the ring plate 30 is reflected on the cornea Ec, and similarly passes on the optical path A2 and is projected to the CCD 45. In this case, as shown in FIG. 5, the ring plate 30 can project a light flux from a central region of the cornea Ec to a peripheral region thereof to the CCD 45 and the ring plate 80 can project a light flux from the central region (extremely central portion) of the cornea Ec thereto.

Then, as shown in FIG. 5, the indexes C1 to C4 and C6 as ring reflection images, the alignment mark M, and the cornea reflection image PR by the stop 72 are displayed together with the anterior eye portion image on the display screen 100 of the monitor 202.

Also, when the cornea shape measurement is conducted, the ring images projected to the CCD 45 are stored in the memory 203, and, for example, a corneal curvature radius is computed from a position relationship among the respective ring images. Thus, an accurate cornea shape is obtained.

Further, data and the like related to a cornea shape etc., are stored in the monitor 203 and these data are printed out together with the image shown in FIG. 5 by the printer 204.

On the other hand, when eye refractive power is measured, mode switching is conducted by the operating means 208. Next, the lamp 11 of the fixed index projecting optical system 10 is turned on to face the eye to be examined in a predetermined direction, and similarly alignment is conducted. When the alignment is completed and a switch which is not shown is pushed, the infrared LED 51 of the eye refractive power measurement index optical system 50 is turned on to project a ring flux to the eye fundus Er. The reflected light is projected to the CCD 45 through the light receiving optical system 60. Eye refractive power is obtained from the ring image by the computation of the control circuit 209.

Note that the light flux through the index 54, for measuring the eye refractive power of the eye to be examined E is projected as shown in FIG. 7. Measurement sensitivity in eye refractive power measurement is determined according to a light flux diameter on the eye to be examined E. Thus, when the sensitivity is improved, it is necessary to increase the diameter of a lens.

Also, when an index for measuring the central region (extremely central portion) of the cornea Ec is projected, it is necessary to locate a ring pattern in a region close to the center of the optical axis A3.

As described above, according to this embodiment mode, a shape from the central region (extremely central portion) of the cornea Ec to the peripheral region thereof can be measured without reducing the sensitivity of eye refractive power measurement. In addition, the measurement becomes possible when the pattern is projected to the cornea of the eye to be examined through the objective lens and the reflected image from the cornea is led to the CCD through the objective lens.

Note that, although the apparatus and the method according to the present invention are described with several specific embodiment modes, various modifications can be made for the embodiment modes of the present invention which are described in this document, by a person skilled in the art without departing from the spirit and scope of the present invention. For example, in the respective embodiment modes described above, the cornea shape index projecting means including the first and second projecting means is integrally provided to the eye refractive power apparatus. However, for example, this means may be integrally provided to an ophthalmologic apparatus such as an eye fundus camera. Further, it is not limited to an ophthalmologic apparatus as a complex machine of a cornea shape measuring apparatus and an eye refractive power measuring apparatus, and may be an ophthalmologic apparatus provided with a cornea shape measuring apparatus, an eye refractive power measuring apparatus, and other one or plural various measuring apparatuses. Further, a plurality of second projecting means with any of those structures described above may be provided.

Further, according to the above-mentioned embodiment mode, the second projecting means is constructed such that the infrared LED 71, the stop 72, the relay lens 73, the dichroic mirror 74, and the ring plate 80 for cornea central portion measurement are disposed in this order and the ring plate 80 is located on the optical path A2. However, it is not limited to this. In other words, it may be constructed such that the ring plate 80 is provided between the relay lens 73 and the mirror 74. In this case, the alignment index projecting optical system 70 is used for cornea shape measurement.

INDUSTRIAL APPLICABILITY

As described above, according to the present invention, the measurement area of the cornea is increased while the measurement sensitivity of eye refractive power is kept, and a shape from the central region of the cornea to the peripheral region thereof can be accurately measured without reducing the measurement sensitivity of eye refractive power.

What is claimed is:

1. An ophthalmologic apparatus comprising:
   cornea shape index projecting means for projecting a cornea shape index for measuring a cornea shape of an eye to be examined to a cornea of the eye to be examined;
   an observation optical system for measuring the cornea shape based on an index reflection image reflected on the eye to be examined and observing the eye to be examined; and
   an eye refractive power measurement index optical system partially using an optical path of the observation optical system, for projecting an eye refractive power measurement index for measuring eye refractive power of the eye to be examined to the eye to be examined through the used optical path,
   in which the cornea shape index projecting means includes:
   first projecting means for projecting a first index as a part of the cornea shape index to a peripheral region of the cornea; and
   second projecting means for projecting a second index as another part of the cornea shape index to a central region of the cornea through an optical component of and along the optical path used for at least both the eye refractive power measurement index optical system and the observation optical system.

2. An ophthalmologic apparatus according to claim 1, wherein the first index in the first projecting means is formed from a first ring pattern composed of a plurality of rings with a substantially concentric shape, and
   that the second index in the second projecting means is formed from a second ring pattern composed of a ring with a smaller diameter than at least a smallest diameter ring of the first ring pattern.

3. An ophthalmologic apparatus according to claim 1 or claim 2, wherein the first projecting means includes a first plate for forming the first index, and
   that the first plate has a hole portion which allows to transmit a light flux for measuring the eye refractive power in the central region.

4. An ophthalmologic apparatus according to claim 1 or claim 2, wherein the second projecting means includes a second plate for forming the second index, which is disposed on the optical path of the observation optical system, and
   that the second plate has a hole portion which allows to transmit an optical axis of the index reflection image in a central region.

5. An ophthalmologic apparatus according to claim 3, wherein a lens is disposed opposite to the hole portion of the first plate on the optical path used for the eye refractive power measurement index optical system and the observation optical system, and
   that the second projecting means conducts projection to the central region of the cornea through the lens.

6. An ophthalmologic apparatus according to claim 4, wherein the second plate of the second projecting means includes at least one ring pattern light transmitting portion, and
   that the ring pattern light transmitting portion is formed such that its diameter becomes at least 1.0 mm or less on the eye to be examined.

* * * * *